United States Patent [19]

Manley et al.

[11] Patent Number: 4,930,679

[45] Date of Patent: Jun. 5, 1990

[54] BRAZING OR SOLDERING JIG FOR DENTAL ATTACHMENTS

[76] Inventors: Robert Q. Manley, 507 Seventh St. West, Palmetto, Fla. 34221; Jerome J. Goodman, 39 Highwood Ave., Tenafly, N.J. 07670

[21] Appl. No.: 274,854

[22] Filed: Nov. 22, 1988

[51] Int. Cl.⁵ .................................................. B23K 3/00
[52] U.S. Cl. ......................................... 228/212; 269/7; 29/160.6
[58] Field of Search ............... 228/212; 29/160.6; 269/7; 433/173, 181, 183

[56] References Cited

U.S. PATENT DOCUMENTS

| | | | |
|---|---|---|---|
| 2,295,201 | 9/1942 | Chayes | 433/181 X |
| 3,442,015 | 5/1969 | Goodman | 433/183 X |
| 4,339,867 | 7/1982 | Reznik | 228/212 |

*Primary Examiner*—Kenneth J. Ramsey
*Attorney, Agent, or Firm*—Ralph R. Roberts; Patrick J. Pinto

[57] ABSTRACT

There are disclosed jigs that are used in the present invention. These jigs are directed to hold and retain left, right and intra-proximal attachment forms prior to and during the soldering of the attachment to a crown. Each jig has a precisely formed head portion sized and shaped to receive and retain a mating engaging portion of the attachment so that the attachment is soldered in a predetermined position to the crown. The jig is made of a high temperature material and has a tail portion that is integral with and extends from the shaped head so that both the jig and the crown may be retained in an investment material during the soldering of the attachment to the crown. The attachments are used for bridges or partial restorations. Preferably the jig is provided with a scored surface to provide an improved gipping surface while imbedded in the investment material during soldering.

20 Claims, 4 Drawing Sheets

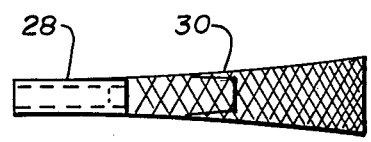
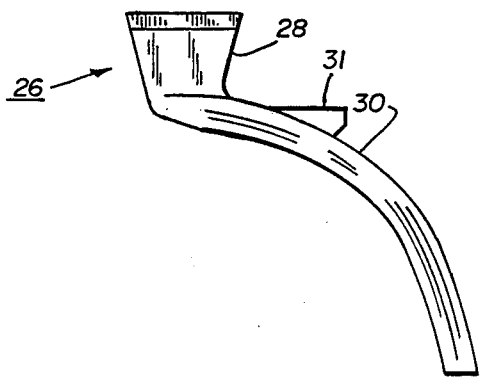
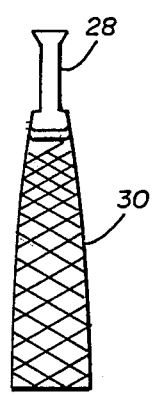
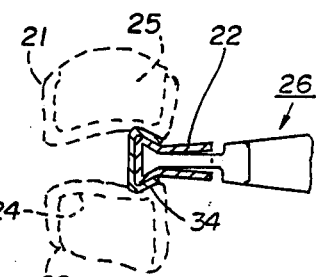
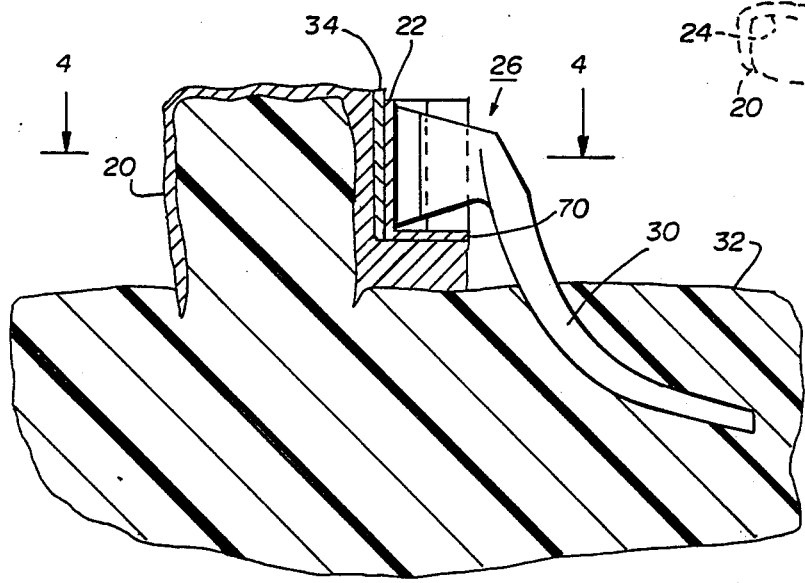

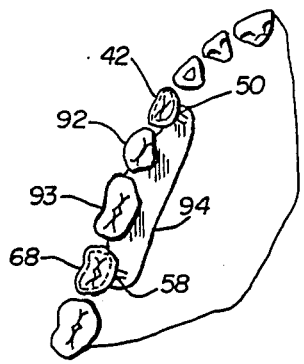
FIG. 8
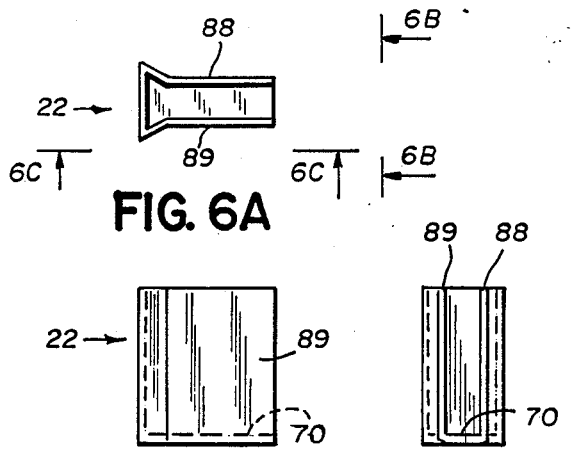
FIG. 6A
FIG. 6C    FIG. 6B
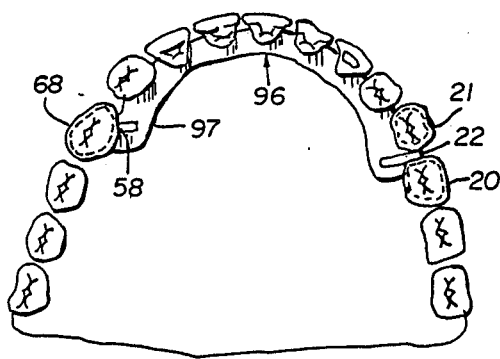
FIG. 9
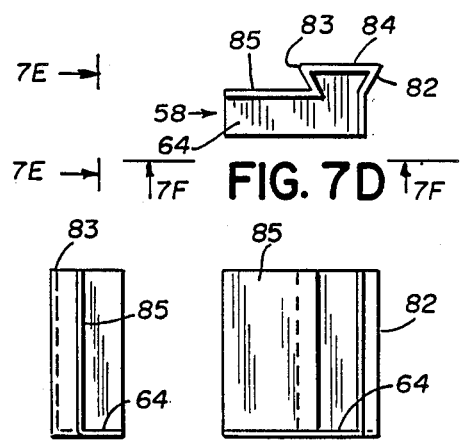
FIG. 7D
FIG. 7E    FIG. 7F
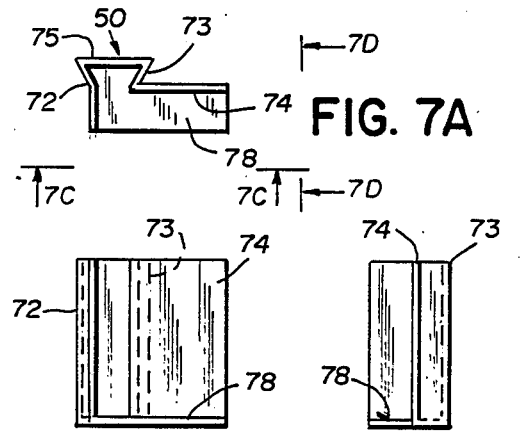
FIG. 7A
FIG. 7C    FIG. 7B

BRAZING OR SOLDERING JIG FOR DENTAL ATTACHMENTS

BACKGROUND OF THE INVENTION

1. Field of the Invention

This invention is believed to be found in the art classified by the U.S. Patent Office as DENTISTRY (Class 433). The jig described and shown below is designed to hold precision (prefabricated) attachments during brazing or soldering procedure, both intra- and extra-coronal attachments. These crowns are utilized for upper and lower prosthetic restoration.

2. DESCRIPTION OF THE PRIOR ART

A careful pre-Ex search in the art was made and found was U.S. Pat. No. 586,023 which issued July 6, 1897 to FLETCHER. This patent was directed to soldering artificial teeth to mouth plates. This device was directed to providing an investment tray which is rotated during soldering. A tooth holder was shown in U.S. Pat. No. 1,496,412 which issued to HAMMANN on June 3, 1924. This patent was directed to holding an artificial tooth adjacent teeth in the mouth of a patient so that a color match is made. U.S. Pat. No. 1,841,870 was issued to VIRIKIAN on Jan. 19, 1932 and showed mounting a denture having insertable portions into a gap that may be present. This denture utilizes a post or pin secured to this restoration to retain an artificial tooth in position.

Also noted was the U.S. Pat. No. 2,469,339 to MANIOLA as issued May 3, 1949. This patent utilized posts or pins to hold teeth which are bored to receive said posts or pins. This removable restoration utilizes natural teeth and the undercut present. Attention is also directed to U.S. Pat. No. 3,231,977 as issued to HARRIS on Feb. 1, 1966. This patent shows apparatus for drilling holes in precise parallelism in a plurality of teeth. This drilling is to provide holes for insertion of cast bridges, etc. These holes provide anchorage for cast restorations. Also of note is U.S. Pat. No. 3,470,935 as issued to Prosen on Oct. 7, 1969. This Patent provides a method of making a dental restoration with one or more porcelain teeth, each with a headed pin.

In the above-noted U.S. Patents, the attention was directed to providing a prosthetic device so as to improve appearance and particularly the efficiency of the teeth in the patient's mouth. The problem of the dentist is to provide an appliance which will properly fit and endure the extreme forces and wear associated with the patients biting and chewing of food. Improvements have been made in both materials and technique to solve these problems. The evolution and/or improvements reflected in the above-noted patents indicate this. A further improvement is believed to be the soldering of a pre-fabricated attachment to a crown with a minimal clearance at and in a precise location. The jigs as shown and described in the following specification and drawings provide a means for holding the attachment in precise relationship to the crown during the soldering procedure.

SUMMARY OF THE INVENTION

This invention may be summarized, at least in part, with reference to its objects. It is an object of this invention to provide, and it does provide, a jig requiring a minimal of clearance between the retaining portion of the jig and its mating attachment so that a minimum amount of refractory paint is required during the soldering.

It is a further object of this invention to provide, and it does provide, a reusable jig disposed to hold in a precise position a precision prefabricated attachment during a soldering of said attachment to a crown.

It is still a further object of this invention to provide, and it does provide, a reusable jig disposed to hold a precision pre-fabricated attachment during soldering of said attachment to a crown and to provide a means for easily removing said jig from the attachment after the soldering procedure.

In the following description and drawings, the soldering and brazing jig of this invention provides a unique design in that this jig has a tailpiece which provides an anchoring and holding device totally sub-gingival to the crown or crowns, while also providing a means for easy removal from the attachment. The holding portion of the jig requires a minimal amount of refractory material to be used in close proximity to the attachment. The three embodiments shown and described hereinafter provide a device designed to retain precision (pre-fabricated) attachments during the soldering procedures. Intra- and extra-coronal attachment is shown. These jigs provide an improvement to standard soldering procedures in that:

(1) a minimal amount of clearance between the jig and attachment permits the use of a superior grade (a high K factor) of refractory paint. Therefore the complete soldering procedure may be completed without accompanying vitrification and difficult divesting procedures. In conventional methods, larger masses of investment are used. The associated thermal and/or mechanical shock may result in fracture, consequential movement, and loss of parallelism;

(2) this jig design provides greater exposure to all of the soldering areas;

(3) with maximal protection of vital areas;

(4) This jig design also provides assurance of integrity of position in:

a. relationship to a crown or bridge;

b. maintenance of parallelism to other attachments in the same bridge;

(5) the ability to trim the pod of investment for maximum exposure without a fear of fracturing investment and (6) a reusability of the jigs.

The jig design of the present invention allow for use on intra-coronal T-type female, i.e., C & L, Stern, Ney, Baker, McCollum, Schatzmann, etc., and extra-coronal, i.e., Dawson, Poveromo, ASC-52, Roach, Ball, Crismani, Dalbo, etc.

The jigs, to be shown and described, are small, reusable and provide a system that minimizes investment usage as well as eliminating the bulkiness of a graphite or introducing and holding a ceramic core, supra-occlusally. In using the soldering jig of this invention, the attachment is placed in position on the crown and adjacent thereto so that a minimum of space therebetween is utilized. The soldering matrix is completed with a high-heat soldering of the attachment to the crown. The attachment investment is prepared in the usual manner and dried before soldering to the crown or crowns. With the use of this jig a minimum of solder is required due to a greater degree of visibility and the ability to accurately place the solder.

These jigs are used to position attachments in a precise relationship to the crowns to which they are soldered. The attachment and crown assembly is held by the jig. The removable prosthesis is provided with the mating attachment and, when finished, the removable denture is retained in a precise position and condition so that slippage and/or discomfort are not present. The typical attachment to be soldered to a crown is shown in the drawings, but is not a patentably distinct member. It is to be noted that the restoration is individually made to suit the mouth and needs of the patient, and the restoration is removable and utilizes permanent teeth which are and have been crowned to provide a fixed anchoring means.

In addition to the above summary, the following disclosure is detailed to insure adequacy and aid in understanding of the invention. This disclosure, however, is not intended to cover each new and inventive concept no matter how it may latter be disguised by variations in form or additions of further improvements. For this reason, there have been chosen specific embodiments of the brazing or soldering jig for dental attachments as adopted for use in the preparation of restorations and showing a preferred means for using said jigs. These specific embodiments have been chosen for the purposes of description and illustration as shown in the accompanying drawings wherein:

BRIEF DESCRIPTION OF THE DRAWINGS

FIGS. 1A, 1B, 1C, and 1D represent views in an enlarged scale, of an intra-proximal jig adapted to precisely hold and retain an intra-proximal attachment having a dovetail configuration;

FIG. 1A representing a side view of the jig for holding an intra-proximal attachment by its dovetail;

FIG. 1B representing a side view of the jig of FIG. 1A and in the same enlarged scale;

FIG. 1C representing a top view of the jig of FIG. 1A and in the same enlarged scale;

FIG. 1D representing a side view, partly in section, and showing the jig as seen in FIG. 1B retaining an intra-proximal attachment substantially contiguous to a prepared crown, the jig and crown precisely positioned and retained in and by an investment material;

FIG. 2A represents a side view of the jig, having a contoured head for holding, by the dovetail portion, a left-hand attachment, said jig having a shouldered recess for receiving an offset portion of the attachment;

FIG. 2B represents a side view of the left-hand jig of FIG. 2A and in the same enlarged scale;

FIG. 2C represents a top view of the left-hand jig, this view taken along line 2C—2C of FIG. 2 B and looking in the direction of the arrows;

FIG. 2D represents a side view, partly in section, and showing this left-hand jig retaining a left-hand attachment substantially contiguous to a prepared crown, this jig and crown is precisely positioned and retained in and by an investment material;

FIG. 3A represents a side view of the jig having a contoured head for retaining a right-hand attachment, by its dovetail portion said jig having an extending leg for receiving an offset portion of the attachment;

FIG. 3B represents a side view of the right-hand jig of FIG. 3A and in the same enlarged scale;

FIG. 3C represents a top view of the right-hand jig, this view taken along 3C—3C of FIG. 3B and looking in the direction of the arrows;

FIG. 3D represents a side view, partly in section, and depicting this right-hand jig retaining a right-hand attachment sustantialy contiguous to a prepared crown, this jig and crown precisely retained and positioned in and by an investment material;

FIG. 4 represents a top view of an intra-proximal attachment retained by the jig of FIG. 1A, said attachment positioned in a formed recess between two adjacent crowns, this view partly diagramatic so as to show the positioning and retention of the attachment in use with a crown;

FIG. 6A, 6B, 6C represent top, face and side views of the intra-proximal attachment as used with the jig of FIG. 1A;

FIG. 6A represents a top view of this attachment carried on the jig as in FIGS. 1D and 4, with the dovetail attachment shown in enlarged scale;

FIG. 6B represents a face view of the attachment of FIG. 6A, this view taken along line 6B—6B thereof and looking in the direction of the arrows;

FIG. 6C represents the side view of the attachment, this view taken on line 6C—6C of FIG. 6B and looking in the direction of the arrows;

FIG. 7A, 7B, 7C, 7D, 7E and 7F represent top, face and side views of left- and right-hand attachments to be positioned on a crown and retained by an appropriate mating jig for soldering;

FIG. 7A representing a top or plan view of the attachment providing a left-hand securing of a restoration in the mouth of the patient;

FIG. 7B representing a face view of a left-hand attachment as in FIG. 7A, this view taken along line 7B—7B thereof and looking in the direction of the arrows;

FIG. 7C represents a side view of the left-hand attachment of FIG. 7A, this view taken on the line 7C—7C thereof and looking in the direction of the arrows;

FIG. 7D represents a top or plan view of the attachment providing right-hand securing of a restoration in the mouth of the patient, this view substantially like FIG. 7A but as a mirror immage thereof;

FIG. 7E represents a face view of the right-hand attachment of FIG. 7D, this view taken on the line 7E—7E thereof and looking in the direction of the arrows;

FIG. 7F represents a side view of the right-hand attachment of FIG. 7D, this view taken on the line 7F—7F thereof and looking in the direction of the arrows;

FIG. 8 represents a plan view, partly diagrammatic, and showing a partial restoration utilizing left- and right-hand attachments for securing the partial restoration in the mouth of the patient and FIG. 9 represents a plan view, partly diagrammatic, and showing a bridge restoration with left-hand and intra-proximal attachments for securing the bridge in the mouth of the patient.

In the following description and in the claims, various details are identified by specific names for convenience. These names are intentend to be generic in their application. Corresponding reference characters refer to like members throughout the several figures of the drawing.

Figure 2B:
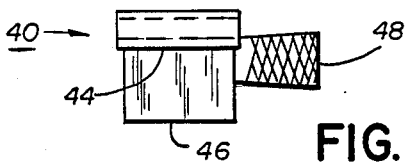
FIGS. 2A, 2B, 2C, and 2D represent views, in the enlarged scale of FIG. 1A, these views of and for a jig adapted to hold and precisely retain a left-hand attachment having, in part, a dovetail configuration.
Figure 2A:
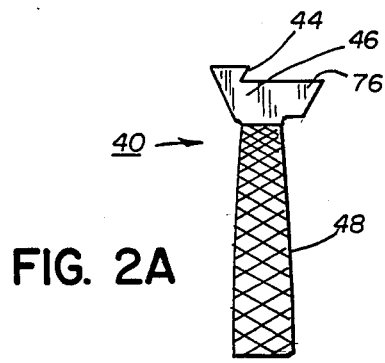
Figure 2C:
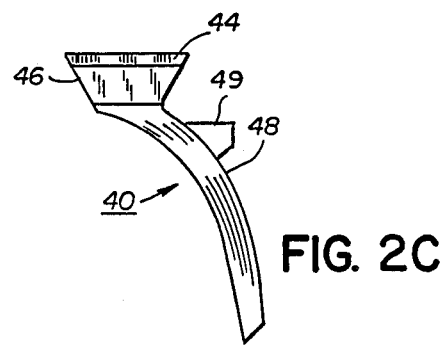

The drawing accompanying, and forming part of, this specification disclose details of construction for the purpose of explanation, but structural details may be modified without departure from the concept and principles of the invention and the invention may be incorporated in other structural forms than shown.

DESCRIPTION OF THE JIGS AND THEIR USE

The jigs employed to maintain the precise relationship of an attachment to a crown are precisely formed. The jigs are intended for holding and maintaining said precise relationship during the soldering of said attachment to a prepared crown. The soldering procedure is performed more efficiently while using a minimum amount of solder.

JIG OF FIGS. 1A, 1B, 1C and 1D

Referring next and now to the drawings, FIGS. 1A, 1B, 1C and 1D depict, in an enlarged scale, a jig to hold and maintain the precise position of an intra-proximal attachment between adjacent crowns. These crowns are cast of metal, such as alloyed gold, used by a dentist to provide suitable rigidity and wear. A crown 20 is shown in cross-section in FIG. 1D. An attachment 22 is held in a precise position and relationship to the crown or crowns. In the showing of FIG. 4, there are shown two adjacent crowns identified as 20 and 21, which have been filled with an investment. Between crowns 20 and 21 is located an attachment identified as 22. This attachment 22 is a snug fit on a jig, generally identified as 26. This jig is a precision casting of a high-temperature metal, such as stainless steel, which material is resistant to the temperatures of soldering. This jig 26 includes a shaped, upper gripping end portion 28 and an integral, curved tailpiece 30 extends therefrom. This attachment 22 is shown in detail in FIG. 6A, 6B, 6C. The attachment 22 as shown in FIG. 1D is diagrammatically depicted as retained in a holding investment material 32, such as a fire-proof molding material, which also is used to simultaneously hold the crowns 20 and 21 in relationship to the attachment 22.

USE AND OPERATION

A master stone model is made of the patients upper and lower jaw. Cast metal crowns 20 and 21 are accurately positioned on the stone model. A recess is accurately ground into the crown or crowns. This recess is contoured to closely match the shape of the attachment to be placed onto the crown(s). It is important and necessary that the bottom of the recess be ground to a predetermined height thereby creating an accurately placed shelf above the patients gum line. The recess is ground to provide a small clearance between the sides of the attachment and the crown.

A technician accurately positions the the attachment into the recess by mounting the attachment on a vertical mandrel. The mandrel is locked into position when the bottom of the attachment is resting on the bottom of the recess. The technician carefully verifies the correct position of the attachment and its relative position to the crown.

After the technician is satisfied with the positioning of the attachment, he or she temporarily secures the attachment to the crown by using a melted wax, such as a sticky wax. After the wax chills and sets, the attachment is bonded to the crown. The placement and temporary securing the attachment to the crown is repeated as necessary and depending on the number of attachments needed to hold a bridge.

The crown and bridge assembly are carefully removed from the stone model. A matching jig of the present invention is selected. The dovetail head portion 28 is dipped or coated in a refractory paint, such as a pattern coat. Each selected jig is placed into the mating portion of the attachment 22. After the jig is fully seated any gaps between the attachment and the jig are filled with the refractory paint. The refractory paint is then allowed to set for a selected amount of time.

A high-heat investment molding material is prepared and molded into the cavity of each crown and around the tailpiece of the jig 22 and allowed to set. After the crown, jig and investment assembly is allowed to set, the technician places the assembly into an oven to harden the investment. The temperature and time is dependent on the type of investment employed.

During the baking process in the oven the wax, holding the attachment to the crown melts leaving a small gap between the attachment and the crown. The attachment is now held by the jig and the pattern coat. After the baking period is completed, the crown, attachment, jig and investment assembly is removed from the oven and allowed to cool.

The technician prepares the attachment for soldering to the crown by applying a small amount of flux 34 into the small clearance between the attachment and the crown. The attachment is then soldered to the crown. The jig maintains the exact precise positioning of the attachment to the crown, that the technician originally set up, because the crown and jig are held in precise relationship by the hardened investment material.

The assembly is cooled following the soldering procedure and subsequently the technician breaks away the investment from the crown and the tail of the jig. The jig is removed from the attachment. If the jig is difficult to remove, the technician uses a hammer or impact tool to bear against the v-groove between the lug 31 and the tail piece 30.

The crown-attachment assembly is cleaned and prepared for further processing such as Porcelain coating.

EMBODIMENT OF FIGS. 2A, 2B, 2C AND 2D

FIGS. 2A, 2B, 2C and 2D shows and discloses a jig generally identified as 40. This jig 40 may be designated as "left-hand" and is contemplated to secure and retain an attachment having a small shoulder or flat portion 74. A crown, identified as 42 in FIG. 2D, which has been cast and shaped to approximate the patients tooth, is prepared to accept an accurately placed left-hand attachment 50. The jig 40 is made with a dovetail portion 44 in head portion 46. This head 46 is cast integrally with tailpiece portion 48. The tailpiece portion may or may not have a lug portion 49. Attachment 50 (also in FIG. 7.) which has been precisely located with relation to the crown and temporarily secured by a melted and cooled wax substance is retained in an investment material 32. The jig 50, which has been coated with a refractory paint and assembled into the mating portion of the attachment 50, is also imbedded into the investment material 32. The attachment is then soldered to the crown using the procedure as described in FIG. 1D. This attachment 50 as with other attachments is usually soldered to the crown at a point facing the interior of the patients mouth. The visible portion of the crown is usually has an inlay of porcelain or the like so that the finished crown provides an appearance that at least approaches that of the patients real teeth. As in the attachment noted in FIG. 1D, the attachment 50 is soldered so that a bottom shelf 79 of a ground recess in the crown engages a bottom shoulder 78 of the attachment 50 to ensure precise vertical positioning with other attachments which are employed to retain a partial denture or bridge.

EMBODIMENT OF FIGS. 3A, 3B, 3C AND 3D

In the drawings of FIGS. 3A, 3B, 3C and 3D is depicted a jig generally identified as 60 and will be used with a right- hand attachment 58, which is as seen and depicted in FIG. 8. This jig 60 is a more or less mirror image of the jig of FIG. 2. Jig 60 has a head portion 62 which is adapted to hold and retain an attachment 58 by its dovetail portion 65. This jig 60, like others previously described, has an integral tail portion 66 which is utilized to hold the jig in the investment material 32. The preparation of the crown, is like other crowns previously described in this specification.

It is to be noted that this jig 60 provides retention of the attachment 58 in the exact relationship to the crown during the baking and soldering procedures, as previously described. It is extremely important to maintain the exact positioning of the attachment as set up by the technician during the soldering procedure for ease of alignment and insertion of a bridge by the patient An attachment is soldered to a crown which will engage one of the attaching points of a bridge or partial and therefore requires that all attachments have .Parallel axis and a common bottom stopping point. The tolerances of the fit and placement are very precise and are intended to be one-or two-thousands of an inch. The partial or bridge are fitted with male attachments to engage the female attachments soldered to the crowns. The bridge or partial is also fitted with a friction means such as a light spring to provide a friction engagement with the outside surface of the crown.

EMBODIMENT OF FIG. 4

In FIG. 4, a plan view of the attachment 22 is shown mounted and retained on the jig, generally identified as 26. The formed head portion 28 of the jig engages the attachment 22 so that the dovetail portion of said attachment is fitted to the mating dovetail of head portion 28. The attachment has a stop portion identified as 70, and in FIG. 1 D this stop portion 70 is illustrated as and when the attachment is.and on the head portion 28 and seated into the recess, which is ground or formed in the crown or crowns. The adjacent crowns 20 and 21 are substantially contiguous, and this attachment 22 is fitted and soldered into the recess between the crowns 20 and 21. The crowns 20 and 21 and the jig are retained in place by investment material 32 during soldering of the attachment to the crowns. The jig which has been coated with a refractory paint will not and cannot be soldered to the attachment, because said refractory paint will not permit solder to enter between the attachment and the jig. After the small clearance between the crown and the attachment is treated with a suitable flux 34, solder will fill this clearance and firmly bond the attachment to the crown. The attachment 22 and solder joint is then polished and finished for use in the patients mouth. Jig 26 and attachment 22 are usually used with adjacent crowns requiring an intra-proximal attachment to hold a partial denture or bridge.

EMBODIMENT OF FIGS. 5A AND 5B

Figure 5A:
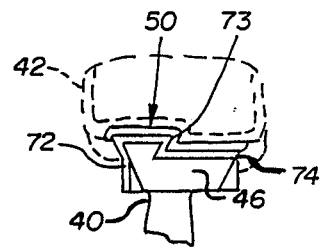
FIG. 5A represents a top or plan view looking downward on a left hand attachment as held by the jig of FIG. 2A for retaining the left-hand attachment during soldering of said attachment to a crown, this view partly diagrammatic so as to show the positioning and retention of the attachment in use with a crown.
Figure 5B:
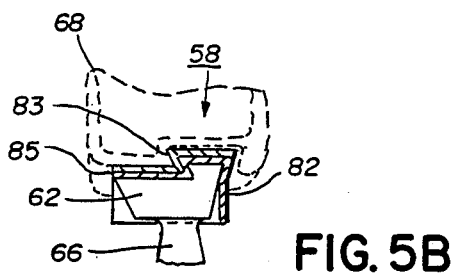
FIG. 5B represents a top or plan view looking downward on a right-hand attachment as held by jig of FIG. 3A, said jig retaining the right-hand attachment during soldering of the attachment to a crown, this view partly diagrammatic to illustrate the desired positioning and retention of the attachment as used with a crown.

In FIGS. 5A and 5B, there are shown left- and right-hand attachments 50 and 58 for securing, by soldering, to a prepared crown. These attachments are usually affixed to a single crown. The patient's dental array usually determines the type of crown-attachment assembly to be used in and with a restoration, partial or a bridge. In FIG. 5A, a left-hand jig 40 is utilized to retain attachment 50 in a precise relationship with crown 42 during soldering. It is to be noted in this view that the attachment 50 has a dovetail formed by sides 72 and 73. A leg portion 74 extends from side 73 and adapted to seat on flat portion 76 of the head 46 of the jig. Attachment 50 is shown in FIGS. 7A, 7B, and 7C and will be described later.

In FIG. 5B, a more or less mirror image of the showing of FIG. 5A is depicted, but as previously noted this attachment is utilized for retention of a right-hand attachment. This right-hand attachment 58 is positioned in and on a recess formed into crown 68. The preliminary steps and procedures prior to the actual soldering of the attachment to the crown and as previously noted and described is followed. It is to be noted that dovetail sides of the attachment 58 are identified as 82 and 83 and mate with the dovetail sides of jig 60. A horizontal leg 85 extends from the dovetail side 83.

ATTACHMENT OF FIGS. 6A, 6B, AND 6C

In FIGS. 6A, 6B and 6C, the attachment of FIGS. 1D and 4 is shown. This is known as a intra-proximal attachment, with the dovetail portion formed by sides 88 and 89, and each of the sides illustrated as .substantially equal, but this a matter of selection and/or choice. The bottom stop portion 70 is shown as integral with the sides and rear wall 90. As previously noted, the stop portion 70 rests against the bottom of the recess which is ground or formed in the crown. The rear wall 90 and sides of the dovetail are normally fitted into said recess with a small clearance. It is important that all attachments are soldered at the same horizontal plane with their vertical axis in a parallel relationship to insure a proper fit of the bridge, partial or restoration.

ATTACHMENT OF FIGS. 7A, 7B, AND 7C

Figure 2D:
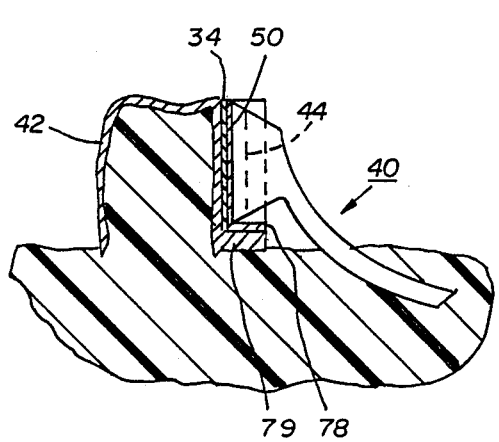

In FIGS. 7A, 7B and 7C, the left-hand attachment 50 Of FIG. 2D and FIG. 5A is shown. The three views depict this attachment before a first securing to a crown, attachment to a jig or soldering to the crown. The dovetail as shown is formed by the rear wall 75 with sides 72 and 73. A leg 74 extending to the right from side 73. A bottom stop portion 78 encloses the bottom of the attachment.

ATTACHMENT OF FIGS. 7D, 7E, AND 7F

Figure 3C:
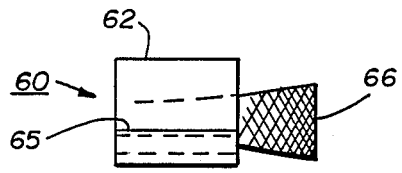
FIG. 3A, 3B, 3C, and 3D, represent views in the enlarged scale of FIG. 1A, these views of and for a jig adapted to hold and precisely retain a right-hand attachment having in part a dovetail configuration.
Figures 3A, 3B:
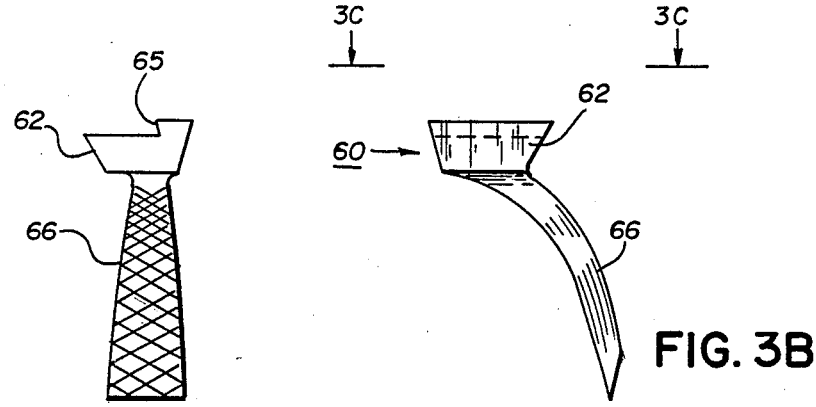
Figure 3D:
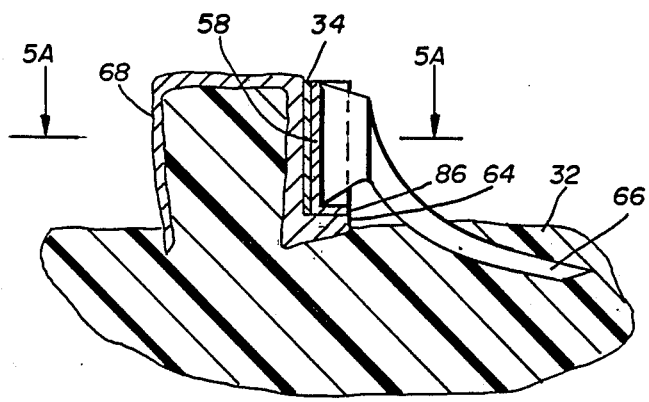

In FIGS. 7D, 7E and 7F, a right- hand attachment 58 is shown, as previously illustrated in FIGS. 3D and 5B.

The three views show this attachment prior to the first temporary securing to the crown, mounting on its mating jig, and soldering to the crown. The dovetail configuration is provided by the rear wall 84, with sides 82 and 83. A horizontal leg 85 extends to the left of the side 83. A bottom stop 64 encloses the bottom of the attachment.

EMBODIMENT OF FIG. 8

FIG. 8 illustrates, in a diagrammatic way, the resulting use of the crowns, made using the jigs of this invention. A bridge, which is removable, comprising two teeth 92 and 93 retained on a plate 94 is attached to two crowns 42 and 68. Crown 42 has attachment 50 precisely and permanently secured thereto. Crown 68 has been permanently fitted with attachment 58 by soldering. The plate 94 has been fitted at each of its ends with male attachments which mate with the attachments 50 and 58. These male attachments are usually fitted to the end of the plate and reinforced to resist bending during use. The crowns 42 and 68 are permanently anchored to a prepared existing tooth in the patients mouth. The partial as well as a bridge denture restorations are designed to be readily inserted and removed from the patient's mouth but when mounted in the mouth, must prevent unwanted shifting and or wear.

EMBODIMENT OF FIG. 9

Referring next, and finally, to FIG. 9, there is shown a bridge for the lower jaw in which the left-side of the bridge is fitted into a right-hand attachment as in FIG. 5 B and FIG. 7. The bridge is identified as 96 and usually has a metal arch or portion 97 extending from left to the right side of the mouth. This arch portion is merely a matter of preference or design. As to whether or not there are natural teeth between crowns depends on the mouth of the patient. As depicted, crown 68 with soldered attachment 58 is permanently secured to the patients existing prepared tooth. The other end of this bridge is fitted into an attachment 22 soldered to crowns 20 and 21. Crowns 20, 21 and attachment 22 are permanently secured to the patients existing prepared teeth. The bridge or plate is fitted with male ends which mate with attachments 58 and 22. Each end of the bridge may be fitted with a friction retaining member which gently applies a frictional pressure against the surface of the crown. The readily removed or inserted bridge must easily engage and seat in the female attachments 58 and 22 and require the precise positioning of the attachments with regard to the vertical axis of the attachments. It is also important that the bottom portions of the attachments be on the same horizontal plane.

The showings of FIGS. 8 and 9 are only illustrative since each restoration is made to suit the patients exact needs. The selection of the type of crown is a matter of satisfying the requirements of the patient. The dentist is required to prepare the teeth to be crowned. The jigs shown and described above are made to insure that all attachments used therewith are precisely held in position before, during and after soldering. Maintaining the precise positioning of the attachments to the crowns is achieved by the use of a closely fitting head portion fitting into the attachment and the use of an integral tailpiece of each jig imbedded in a investment material along with the crown(s). It is this retained condition in the same mass of investment material which assures the accurate and precise positioning.

The jig construction and use, as shown above and described above are believed to suggest and teach a method of constructing and using said jigs and attachments for precisely positioning a female attachment in a contiguous relationship to a associated crown used in dental restorations and the like. The preferred dovetail interior construction has been shown and described above but other female/male engaging configurations are contemplated such as a T-Slot, Key-Hole and the like. Each jig retains the precise positioning of the attachment prior to, during and after soldering said attachment to said associated crown, these steps including;

precisely forming a head portion of a jig, said head sized and shaped to receive and retain said metal attachment having a female interior configuration;

providing an integral tailpiece portion of said jig and utilizing this tailpiece for retention of, placing and positioning of this jig, and supplying a quantity of a relatively fire-proof refractory investment material and with said investment material adapted to retain a prepared crown and the tailpiece portion of the jig so that said crown and attachment may be maintained in a precisely determined position and contiguous relationship prior to, during and subsequent to soldering of the attachment to the crown;

removing said jig from the attachment, and the now soldered in place attachment providing a substantially vertical passageway for and retention of a male attachment portion of a dental restoration.

Terms such as "left", "right", "up", "down", "bottom", "top", "Front", "back", "in", "out", and the like are applicable to the embodiments shown and described in conjunction with the drawings. These terms are merely for the purposes of description and do not necessarily apply to the position in which the brazing or soldering jig for dental attachments may be constructed or used.

While particular embodiments of the soldering jigs have been shown and described, it is to be understood that the invention is not limited thereto and protection is sought to the broadest extent the prior art allows.

What is claimed is:

1. A jig employed to precisely position a metal attachment contiguous to a metallic crown as used by dentists for restorations and the like, this jig retaining said attachment prior to and during the soldering of the attachment to the crown, this jig including:

(a) a precisely formed head means sized and shaped to receive and retain the metal attachment having a selected engaging configuration;

(b) an integral tailpiece portion of said jig adapted for retention in an investment of relatively fireproof material adapted to retain said crown and the tailpiece portion of the jig; said jig being adapted to maintain said crown and attachment in a contiguous relationship prior to and during the soldering of the attachment to said crown.

2. A jig for holding an attachment as in claim 1, in which said jig is of a metal, such as stainless steel, and having a high-temperature melting property and having little or no distortion during said soldering of the attachment to said crown.

3. A jig for holding an attachment, as in claim 2, in which the integral tailpiece is curved and contoured so that, when mounted in a desired position in the investment, the attachment and a dovetail engaging portion thereof are retained substantially parallel to the vertical axis of the crown.

4. A jig for holding an attachment, as in claim 3, in which the jig is adapted for retaining a right-hand female attachment.

5. A jig for holding an attachment, as in claim 3, in which the jig is adapted for retaining a left-hand female attachment.

6. A jig for holding an attachment, as in claim 3, in which the jig is adapted for retaining an intra-proximal female attachment.

7. A jig for holding an attachment, as in claim 3, in which the curved tailpiece is formed with a substantially rectangular cross-section and with one of the broader surfaces having a scored surface for providing a retaining grip in the investment.

8. A jig for holding an attachment, as in claim 3, in which said head portion of the jig is formed with a shoulder adapted to receive and retain said attachment and the configuration thereof so that the axis of the dovetail portion is disposed in an alignment with the axis of the crown to which said attachment is to be soldered.

9. A jig for holding an attachment, as in claim 8, in which the head means is also formed so that a stop shoulder portion of the attachment is engaged by said head means so that precise vertical positioning is established.

10. A jig for holding an attachment, as in claim 5, in which said head means of the jig is formed with a shoulder adapted to receive and retain said attachment and the configuration thereof so that the dovetail portion is disposed in an alignment with the axis of the crown to which said attachment is to be soldered.

11. A jig for holding an attachment, as in claim 10, in which the head means is also formed so that a stop shoulder portion of the attachment is engaged by said head means so that precise vertical positioning is established.

12. A jig for holding an attachment, as in claim 3, having a lug portion formed along with said tailpiece and together forming a means for use in removing said jig from said attachment after soldering.

13. A method of constructing and using a jig and attachment for precisely positioning a metal attachment in a contiguous relationship to an associated crown used in dental restorations and the like, said jig retaining said attachment prior to, and during the soldering of said attachment to said associated crown, said method including the steps of:

(a) precisely forming a head portion of a jig, said head sized and shaped to receive and retain a metal attachment having a selected engaging configuration;

(b) providing an integral tailpiece portion of said jig and utilizing this tailpiece for placing, positioning, and retention of this jig;

(c) supplying a quantity of an investment of relatively fireproof material and with said investment material adapted to retain a prepared crown and the tailpiece portion of the jig so that said crown and attachment may be maintained in a precisely determined position and contiguous relationship to the crown, (d) removing said jig from the attachment, and the now soldered-in-place metal attachment providing and engaging means for retention of a male attachment portion of a dental restoration.

14. A method of constructing and using a jig for holding an attachment, as in claim 13, which includes making said jig of metal such as stainless steel, this metal having a high-temperature melting property and with little or no distortion during heating to a soldering temperature.

15. A method of constructing and using a jig for holding an attachment, as in claim 14, which includes forming said jig with an integral tailpiece which is curved and contoured so that, when mounted in a desired position in an investment mold, provides retaining means for said attachment and the dovetail portion thereof so, with soldering, the attachment is maintained in a substantially vertical axis.

16. A method of constructing and using a jig for holding an attachment, as in claim 15, which includes forming said jig for retaining a right-hand attachment.

17. A method of constructing and using a jig for holding an attachment, as in claim 15, which includes forming said jig for retaining a left-hand attachment.

18. A method of constructing and using a jig for holding an attachment, as in claim 15, which includes forming said jig for retaining an intra-proximal attachment.

19. A method of constructing and using a jig for holding an attachment, as in claim 15, which includes forming said curved tailpiece with a substantially rectangular cross-section and with a scored major surface, and providing a retaining grip into the investment mold.

20. A method of constructing and using a jig for holding an attachment, as in claim 15, which includes forming a notched lug on said tailpiece for removing of the jig from the attachment after soldering the attachment to the crown.

* * * * *